United States Patent

Muszak et al.

Patent Number: 5,419,871
Date of Patent: May 30, 1995

[54] ANALYZER ELEVATOR ASSEMBLY

[76] Inventors: Martin F. Muszak; Alexander W. Hirsch; Michael W. LaCourt, all of Eastman Kodak Company, Rochester, N.Y. 14650

[21] Appl. No.: 236,908
[22] Filed: Apr. 29, 1994
[51] Int. Cl.[6] .......................................... G01N 35/04
[52] U.S. Cl. ......................................... 422/63; 422/64; 422/104; 436/43; 436/44; 436/46; 436/47; 436/48
[58] Field of Search .................... 422/63–66, 422/104; 436/43, 44, 46, 48, 47

[56] References Cited

U.S. PATENT DOCUMENTS

| | | | |
|---|---|---|---|
| 4,296,070 | 10/1981 | Montalto | 422/65 |
| 4,512,952 | 4/1985 | Blanding | 422/65 |
| 4,855,109 | 8/1989 | Muraishi et al. | 422/63 |
| 4,857,272 | 8/1989 | Sugaya | 422/65 |
| 5,055,262 | 10/1991 | Sakagami | 422/64 |
| 5,071,625 | 12/1991 | Kelln et al. | 422/72 |
| 5,075,079 | 12/1991 | Kerr et al. | 422/64 |
| 5,122,342 | 6/1992 | McCulloch et al. | 422/65 |
| 5,219,526 | 6/1993 | Long | 422/64 |
| 5,232,665 | 8/1993 | Burkovich et al. | 422/65 |
| 5,332,549 | 7/1994 | MacIndoe, Jr. | 422/63 |

Primary Examiner—James C. Housel
Assistant Examiner—Long V. Le
Attorney, Agent, or Firm—Dana M. Schmidt

[57] ABSTRACT

An analyzer and an elevator therein for moving a slide element from a distributor operating preferably in a single horizontal plane, to one of plural incubators disposed at different vertical levels. A drive mechanism is provided for raising and lowering the elevator, and a pusher is provided, such as a pusher blade within the elevator, to push a slide element from the distributor to a support in the elevator, and then into one of the incubators.

15 Claims, 13 Drawing Sheets

ANALYZER ELEVATOR ASSEMBLY

FIELD OF THE INVENTION

This invention relates to an elevator used to lower a slide element from one part of an analyzer to an incubator at a lower level, and/or to raise it to an incubator at a higher level, particularly for use with stacked incubators.

BACKGROUND OF THE INVENTION

As analyzers become larger and larger to handle more and more tests per hour, it becomes necessary to have more than one incubator to receive sample-bearing slide test elements to incubate them, for higher through-put. See, for example, U.S. Pat. No. 4,512,952, FIG. 1, by D. L. Blanding et al. However, the more incubators that are required, the larger the "foot-print" of the analyzer. Compare, e.g., the footprint of a three-incubator analyzer of the '952 patent, with the footprint of a two-incubator analyzer as shown in U.S. Pat. No. 4,296,070.

The through-put of said '952 patent analyzer is roughly about 700 test elements per hour. To expand this to 1,000 or more places even greater burdens on the analyzer, such as larger or more numerous incubators. Hence, the foot-print tends to become larger still. Larger foot-prints are unacceptable in crowded laboratories.

Thus, there has been a problem in increasing the through-put of the analyzer above, say, 700 slide elements per hour, without drastically increasing the foot-print.

In a related, commonly-owned application cofiled herewith by James Miller, entitled Twin Roter Incubator Assembly U.S. application Ser. No. 08/235,041, a solution to that problem is provided by stacking one incubator generally above the other. However, once that is done, there remains the problem of loading slide elements into those stacked incubators. The traditional mechanism for loading the incubators of the '952 and the '070 patents is to use a rotating slide distributor. To do this at two different levels would require the slide distributor to have a vertical motion as well as a rotary motion. Because of the size of the slide distributor and its mass, such additional degree of freedom in its motion is not deemed to be practical.

Thus, the problem addressed by this invention is to allow the use of vertically-stacked incubators without also requiring the rotating slide distributor to move up and down as well, to the levels of the stacked incubators.

SUMMARY OF THE INVENTION

We have constructed a design that solves the aforesaid problem.

More specifically, there is provided, in one aspect of the invention, a combination of an analyzer incubator for incubating test elements, and an elevator assembly for positioning and loading test elements from a first position adjacent to the incubator to a second position above or below the incubator; the incubator comprising a plurality of sites disposed circumferentially for supporting a test element; and the elevator comprising a support, means for lowering or raising the support from the first position to the second position, and for raising or lowering the support, respectively, and a pusher for pushing a test element onto the support and from the support into the incubator.

In accord with another aspect of the invention, there is provided an analyzer for the analysis of analytes in biological fluids, the analyzer comprising a first and a second incubator disposed one above the other, and a slide distributor for moving slide test elements in a fixed horizontal plane to a position adjacent one of the incubators, and further including an elevator for raising and lowering a test element relative to the distributor and relative to first and second loading positions adjacent the incubators, the elevator including a support and a pusher for pushing a slide element from the distributor onto the support and from the support into either of the incubators.

Accordingly, it is an advantageous feature of the invention that an analyzer is provided with vertically stacked incubators and a mechanism for loading them at different heights, without requiring the distributor that normally moves the slides around, to also go up and down to those different height locations of the incubators.

A related advantageous feature is that the mechanism allowing for loading of a slide element at the different heights of the vertically stacked incubators, is simplified in that it need only provide vertical motion to those different heights and horizontal motion into the incubator(s).

Other advantageous features will become apparent upon reference to the detailed Description of the Preferred Embodiments, when read in light of the attached drawings.

DETAILED DESCRIPTION OF THE PREFERRED EMBODIMENTS

The invention is hereinafter described by reference to the preferred embodiments, in which two incubators are stacked together, one vertically above the other for use in an analyzer with a preferred kind of slide distributor and preferred kinds of slide test elements. In addition, the invention is useful regardless of whether there is one or two incubators, or the type and construction of each of the incubators, the slide distributor, or the slide test elements, provided an elevator is used that is separate from the slide distributor, to move the test elements vertically relative to the position of the slide distributor.

Various orientations described herein, such as "upper", "lower", "above", "horizontal", "vertical" and the like refer to the orientations during their preferred use.

Figure 1:
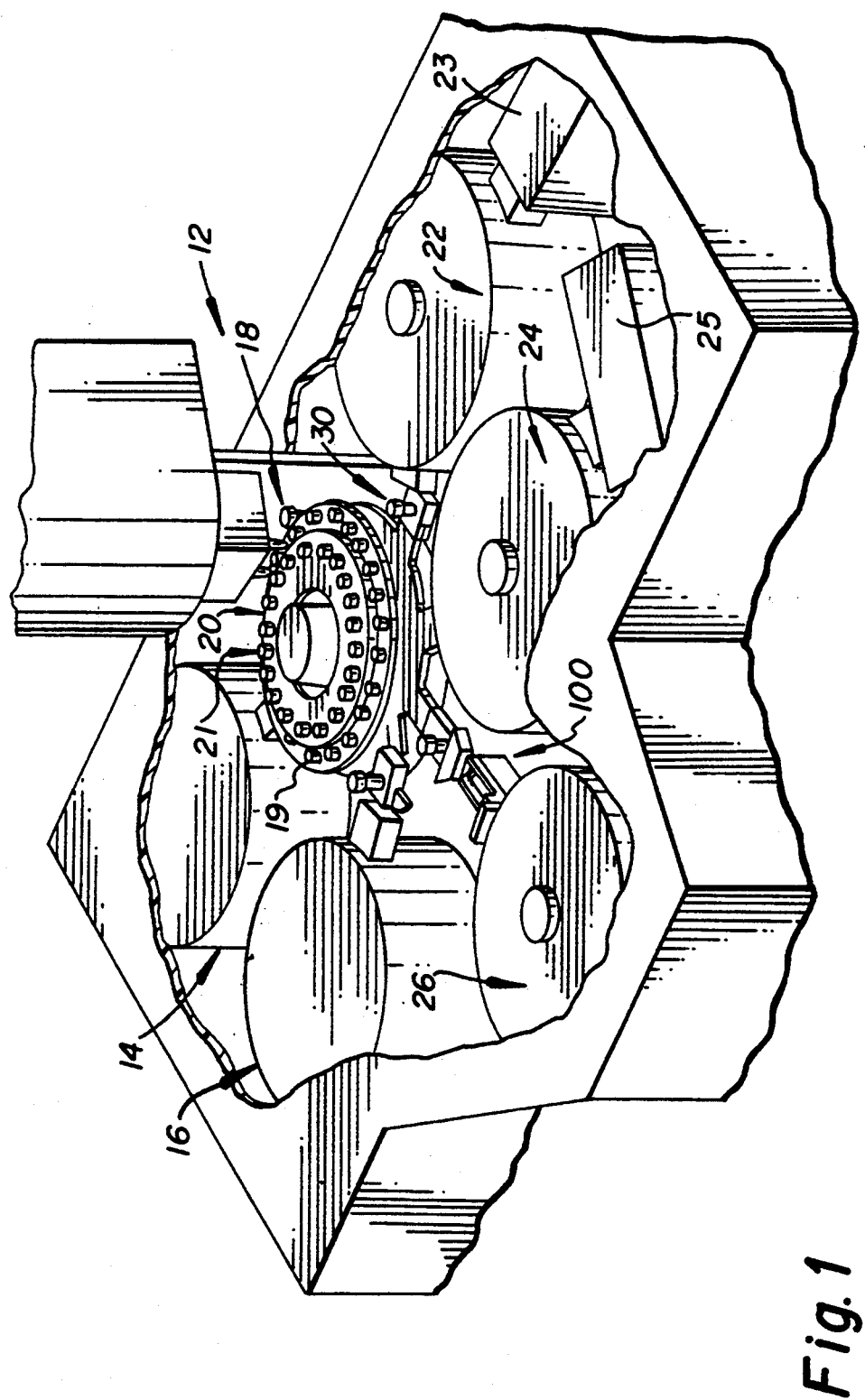
FIG. 1 is a fragmentary isometric view of an analyzer constructed with the elevator of the invention.

The environment of use of the invention is in an analyzer such as, but not limited to, that shown in FIG. 1, in which analyzer 12 has one or more supplies of slide test elements at stations 14 and 16, a supply of patient samples 19 and of disposable tips 21 at a rotating station 20, an aspirating and dispensing tower 18 adjacent station 20, a distributor arm 30 under station 20 to receive slide test elements to move them to tower 18 and to various incubators, at least three incubators 22, 24 and 26 for incubating slide elements received from distributor 20, and readers 23 and 25 of incubated slide elements optionally disposed to one side of the incubators, all as described in, e.g., U.S. Pat. No. 4,512,952. Representative examples of these features can be found in, e.g., those already in use on the analyzer available under the trademark "Ektachem E700" ® manufactured by Eastman Kodak Co. For this reason, the slide elements are preferably the colorimetric type that produce a color signal for detection, and the potentiometric types, both available under the trademark "Ektachem" ® slides from Eastman Kodak Co.

In this invention, as described in the aforesaid related application Ser. No. 08/235,041 incubator 26 is replaced with a pair of stacked incubators 36 and 40 more clearly shown in FIG. 2. Any kind of incubator structure, including conventional structures, can be used for incubators 36 and 40, as well as for their mounting, as they do not constitute part of this invention. Accordingly, they are not further described, except that a single peripheral station 46 and 50, respectively, is shown out of the plural peripheral stations present for each, broken away to illustrate the presence of a hard stop or reference surface 48, at each station 46, that abuts against a datum reference edge 52 of slide element E that is incubated in incubator 36 on a support 49. No such reference surface is provided on support 51 at stations 50 for slide elements E'. The reason is, FIG. 3, elements E' are ejected from stations 50 by pushing them through the station into a stationary dump 53 located inside of rotating supports 51.

Figure 3:
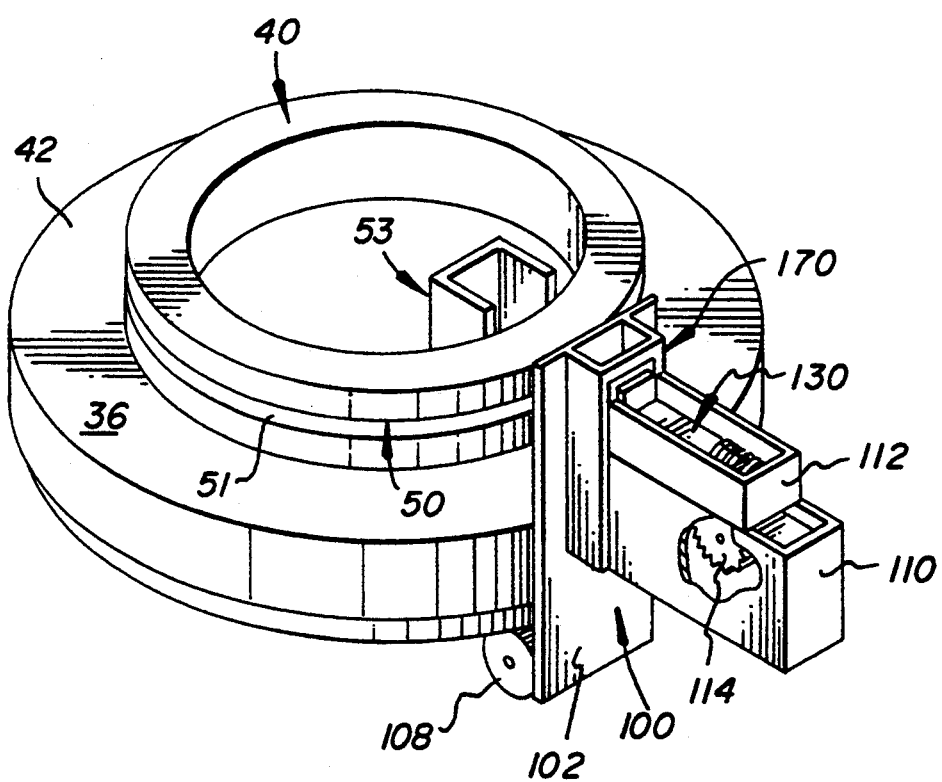
FIG. 3 is an isometric view of the two stacked incubators and elevator of FIG. 2.

It will be noted from FIG. 3 that incubator 40 is directly above incubator 36, although their respective rotor centers need not be vertically aligned. As used herein, one incubator is directly above the other if the vertical projection upward of the footprint of the other totally encompasses the footprint of the one (as shown). Conveniently, incubator 40 can be mounted on a cover 42 used for incubator 36, the details of which are omitted.

Also, it is noted that incubator 36 is preferably, but not necessarily, dedicated to colorimetric type of slide test elements E, that is, those that produce a color change. Incubator 40 on the other hand is preferably, but not necessarily, dedicated to potentiometric type slide test elements E' that produce a differential voltage. Thus, slide elements E and E' are selected accordingly.

Figure 2:
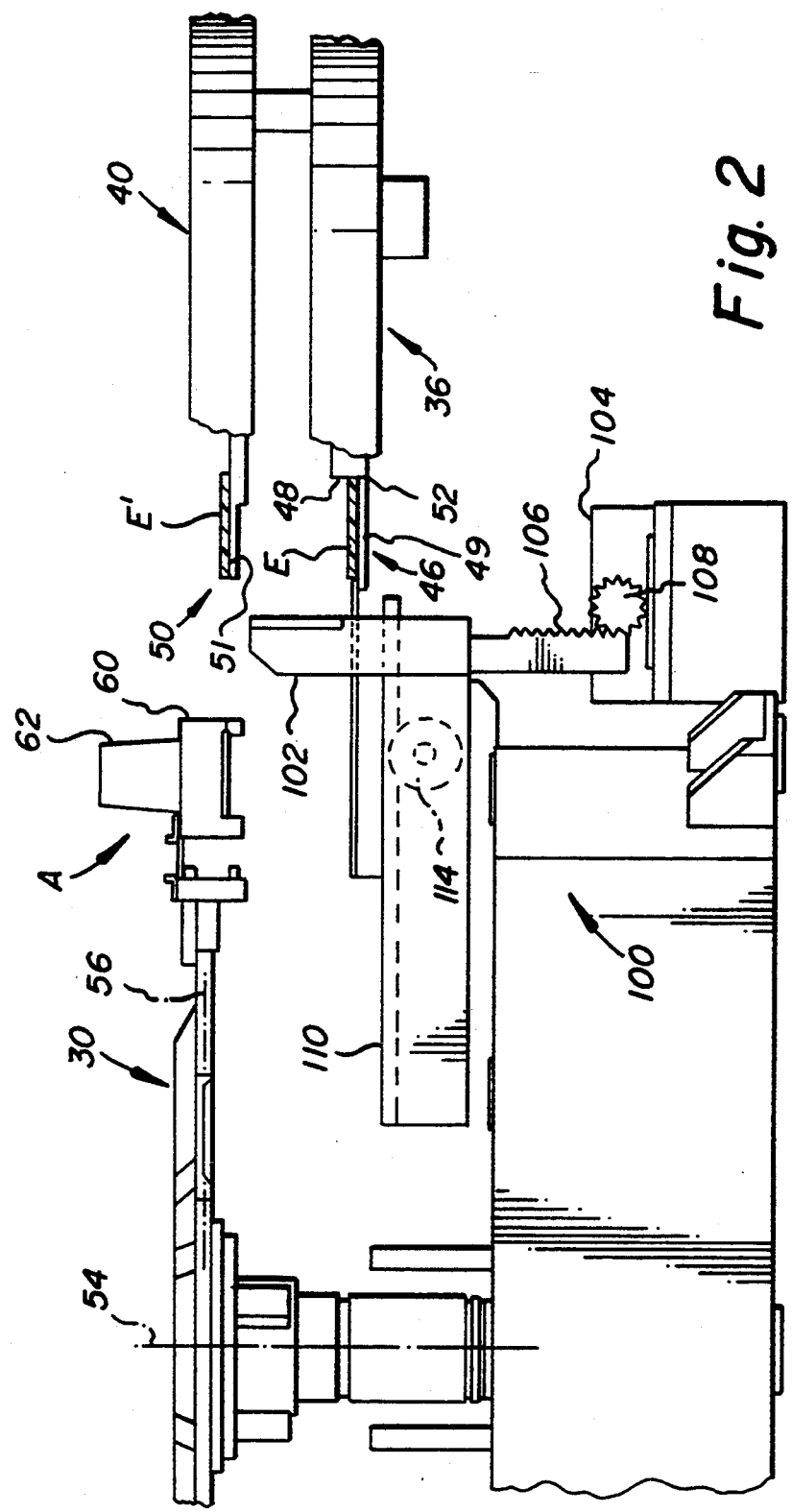
FIG. 2 is a fragmentary elevational view, partially broken away, of a portion of the analyzer depicting the slide distributor, two stacked incubators, and the elevator servicing those incubators.

As is conventional, slide distributor 30, FIG. 2, rotates about an axis 54 in a single horizontal plane 56 to supply slide test elements E and E' to a position A that is adjacent incubators 36 and 40, and most particularly, in the plane of slide support 51 at station 50 of incubator 40. It is not, however, capable of moving out of plane 56, that is, it cannot move down to the level of support 49 of incubator 34.

Distributor 30 has a slide block 60 at the end of each of its arms to temporarily hold a slide element E or E', and a metering housing 62 there-above to aid in dispensing sample or reference fluid onto element E or E', also as is conventional.

In accordance with the invention, an elevator assembly 100 separate from the slide distributor 30 is provided to move slide test elements E down to the level of support 49 of incubator 36. It also functions to permit elements E' to be loaded into incubator 40 from distributor slide block 60.

Figure 4:
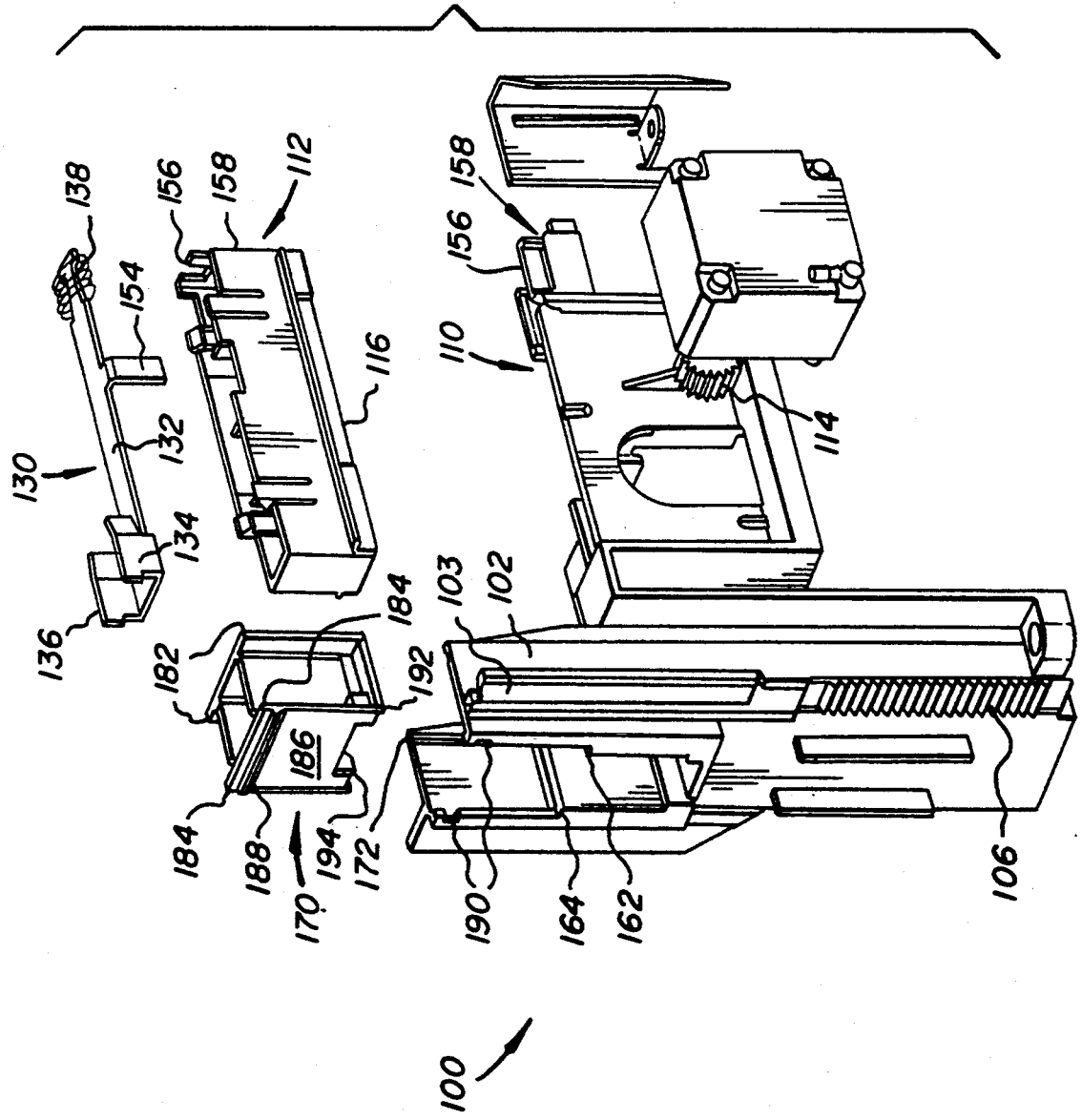
FIG. 4 is an exploded isometric view of the elevator structure.
Figure 8:
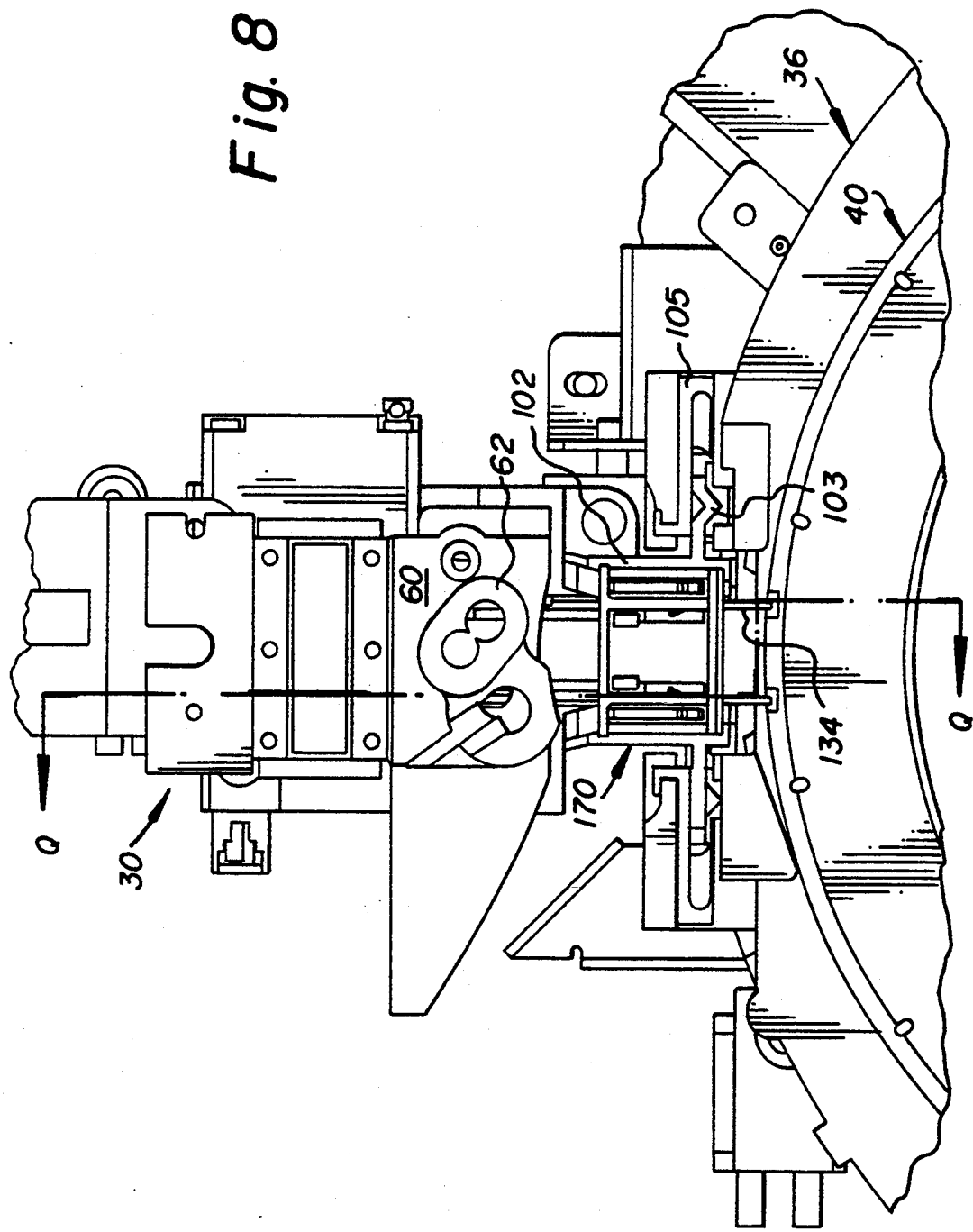
FIG. 8 is a fragmentary plan view of the elevator engaged with the distributor slide block.
Figure 9:
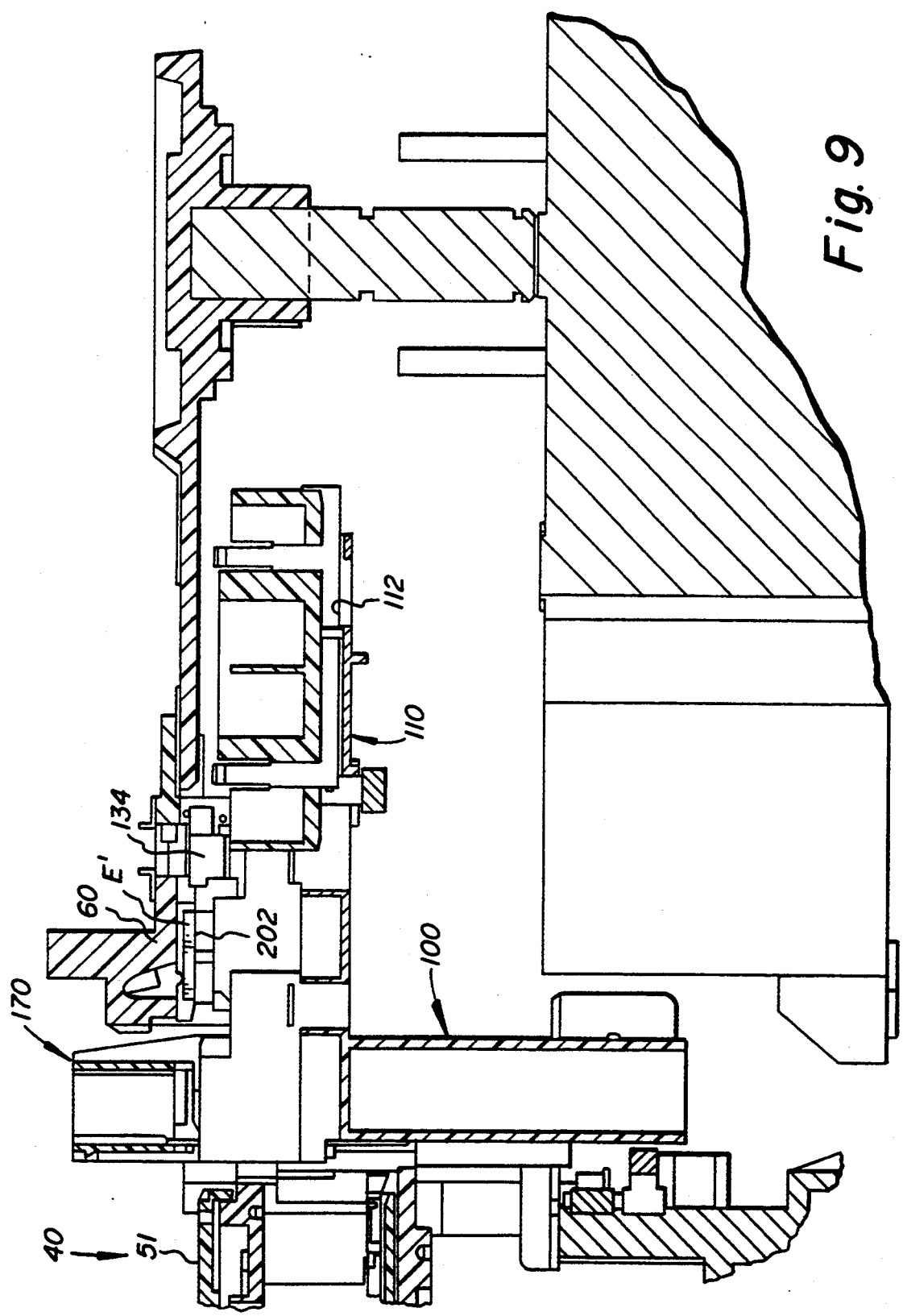
FIGS. 9-14 are section views taken generally along line Q—Q of FIG. 8, except that the elevator is shown moving through its various stations (FIG. 11 being an exact section view along line Q—Q)

To provide up and down movement, elevator 100 preferably comprises, FIG. 4, a vertical frame 102 having a guide flange 103 that rides between a bearing block 105, FIG. 8, a motor 104, FIG. 2, for raising and lowering frame 102 and flange 103 via a rack 106 and a pinion gear 108, a horizontal track 110, a carrier 112 for a pusher 130 shown more clearly in FIG. 4, a pinion gear 114 for driving carrier 112 via a rack 116 projecting down through track 112, and a cover 170 described hereinafter in detail. (Other conventional raising and lowering mechanisms can be used in place of frame 102, motor 104 and rack and pinion 106, 108—see for example the embodiment of FIG. 15.)

Figure 5:
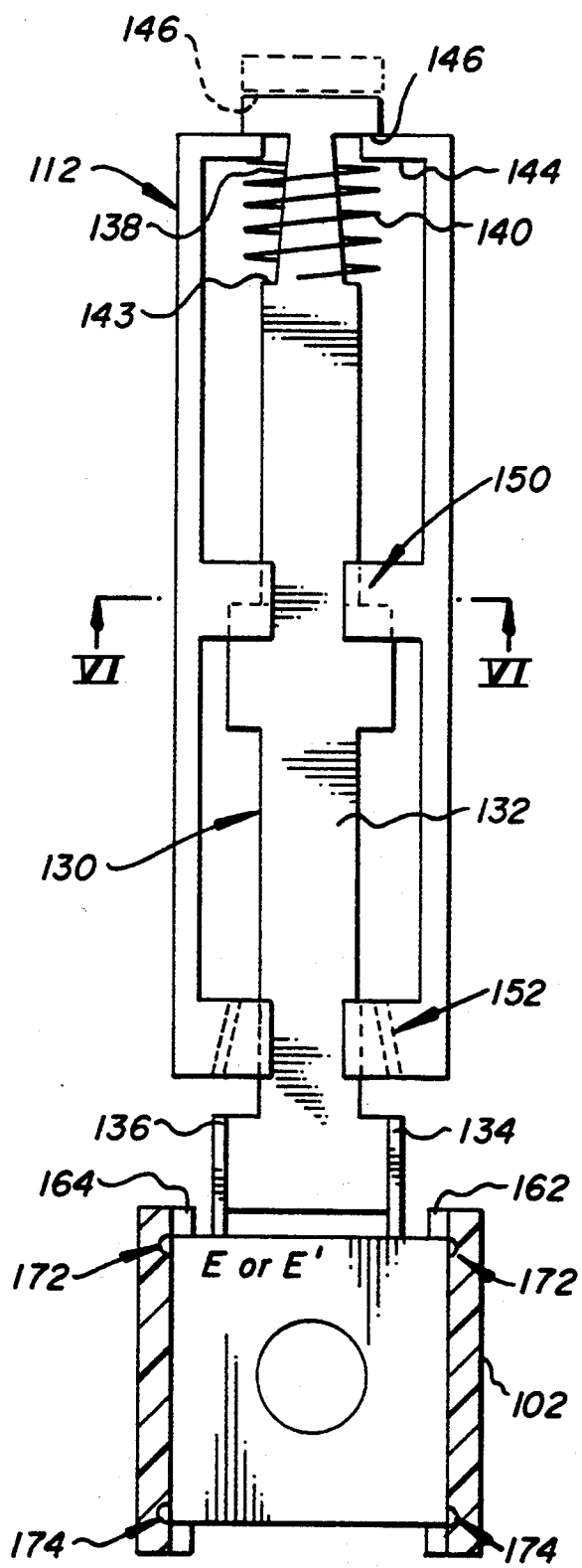
FIG. 5 is a top plan view, partly in section, of the elevator structure shown in FIG. 4, and a slide element engaged by the elevator.

Pusher 130 preferably comprises, FIG. 4, a blade mechanism featuring a horizontally extending body 132, a pair of pusher fingers 134, 136 at one end of body 132, and a spring-retaining notch 138 at the opposite end. A compression spring 140, FIG. 5, is mounted around notch 138 to press against surface 143 of notch 138, and against end surface 144 of carrier 112. Opposite surface 146 of notch 138 keeps blade 130 from advancing too far within carrier 112.

Figure 6:
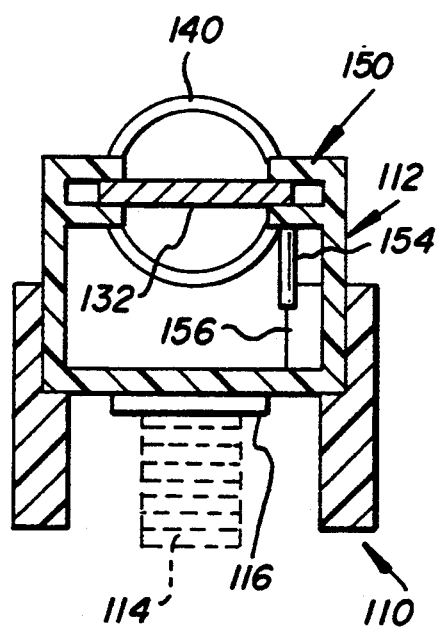
FIG. 6 is a section view taken generally along the line VI—VI of FIG. 5.

Body portion 132, FIGS. 5 and 6, slides between and is retained by one or more pairs of lips 150, 152 of carrier 112, under the action of spring 140, as described further hereinafter.

To ensure blade 130 does not stick within lips 150, 152 to render ineffective the action of spring 140, a release lug 154 can be included, FIG. 4, to press against a fixed stop 156 disposed near end 158 of track 110. See also FIG. 6.

Other configurations of the pusher 130 can also be used. For example, the elongated blade can be replaced with a solid bar, a flexible blade, or with a cam mechanism (not shown) having a long enough throw to push the slide element far enough.

Frame 102 includes a slide support, FIGS. 4 and 5, which is preferably two rails 162, 164 spaced apart a distance effective to allow passage of pusher fingers 134, 136 between them. A slide element E or E' is supported on rails 162, 164, FIG. 5, either for movement through frame 102 without stopping, if in element E', or for resting on rails 162, 164 to allow for lowering of the element to incubator 36, in the case of elements E.

Figure 7:
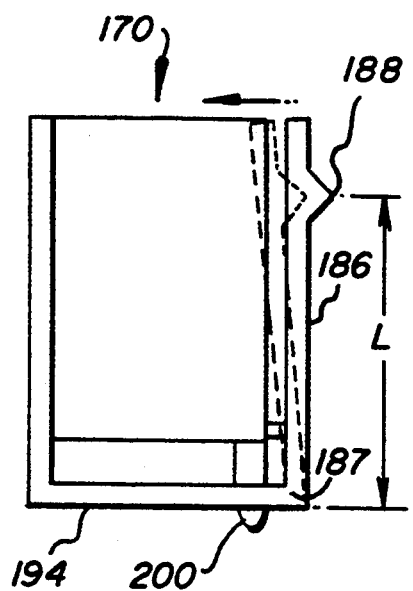
FIG. 7 is a side elevational view of the cap of the elevator shown in FIG. 4.

A cover 170, FIGS. 4 and 7, is preferably included disposed within frame 102 above rails 162, 164. To receive cover 170, two pairs of opposed notches 172, 174 extend upwardly from support rails 162, 164, FIG. 5, and these mate with projecting pairs of side flanges 182, 184, respectively, of cover 170, FIG. 4. Flange 184 in turn is part of a front plate 186 which is cantilevered from the rest of cover 170 at 187, FIG. 7, to provide plate 186 with a degree of flexibility as shown by the phantom position. A shoulder 188 projects outward from plate 186 to snap into place in a mating groove 190 formed at two sides of frame 102, FIG. 4. Plate 186 flexes to the phantom position, FIG. 7, when cover 170 is inserted within grooves 172, until shoulder 188 slides into grooves 190.

A pair of bottom rails 192, 194 is provided on cover 170, FIGS. 4 and 7, and the distance "L", FIG. 7, of these rails from shoulder 188 is preferably controlled so that rails 192, 194 are spaced above matching element support rails 162, 164, FIG. 4, just the correct amount for the height of one slide element E or E', thus preventing two elements from being inadvertently stacked onto rails 162, 164.

Optionally, and preferably, to keep a test element E or E' that is being pushed by blade 130, from advancing too far onto rails 162, 164, that is, so as to stick out beyond front plate 186, anti-skid bumps 200 are included at the bottom of each rail 192, 194, FIG. 7. These keep slide elements E and E' back of front plate 186 and in contact with pusher blade fingers 134 and 136.

It is the function of elevator 100 to insert itself into a slide block 60 of distributor 30, FIG. 8, and to push a slide element therein out to one of the incubators, as is more clearly shown in FIGS. 9–14. Thus, in FIG. 9, elevator 100 has been raised to its highest position and carrier 112 has been withdrawn to its most rearward position, so as to be under and inside the support 202 of slide block 60 holding a slide element E'. Pusher fingers 134, 136 are in position to engage element E', in the same plane of support 202 as support 51 of incubator 40.

Figure 10:
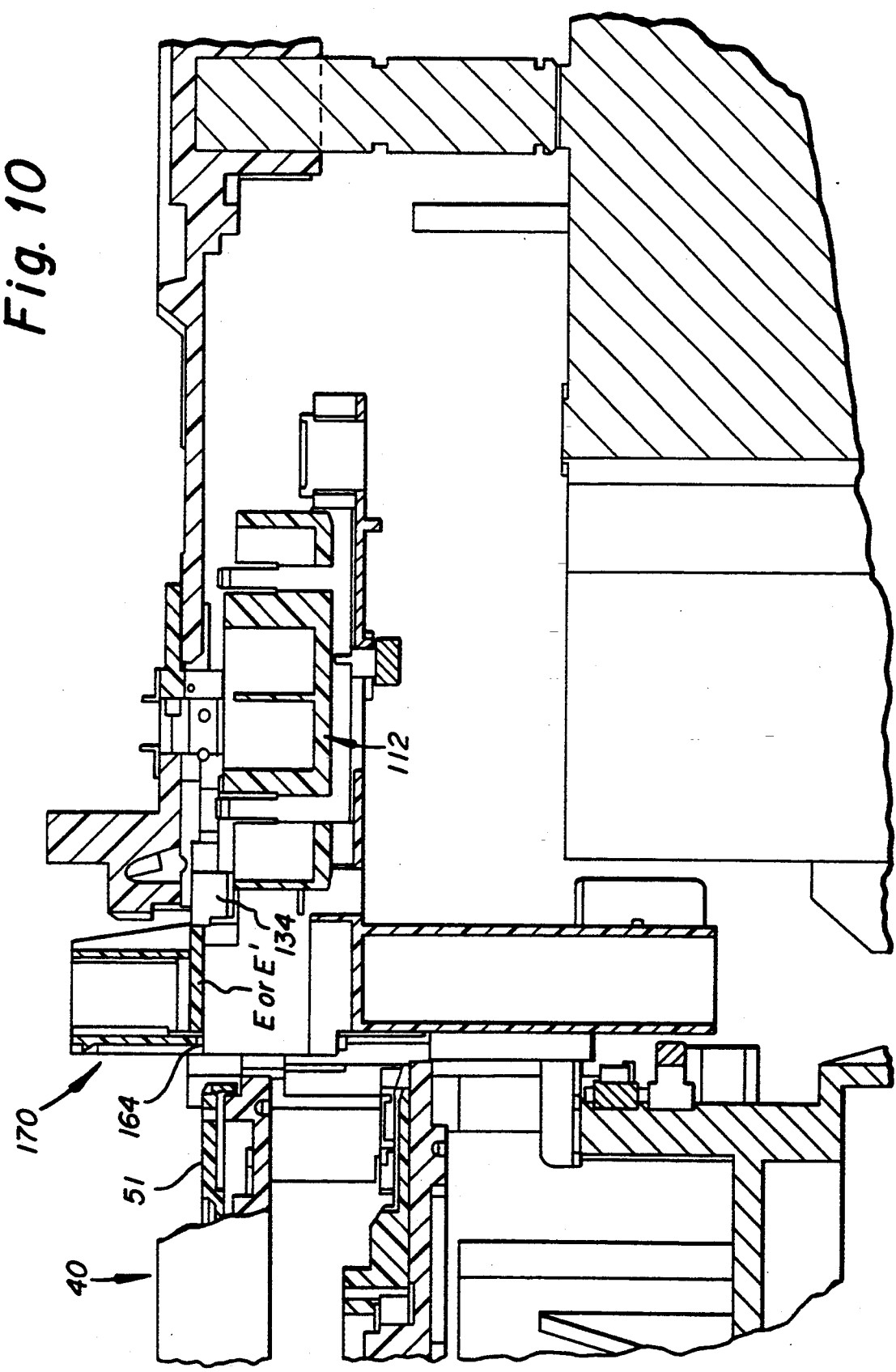
Figure 11:
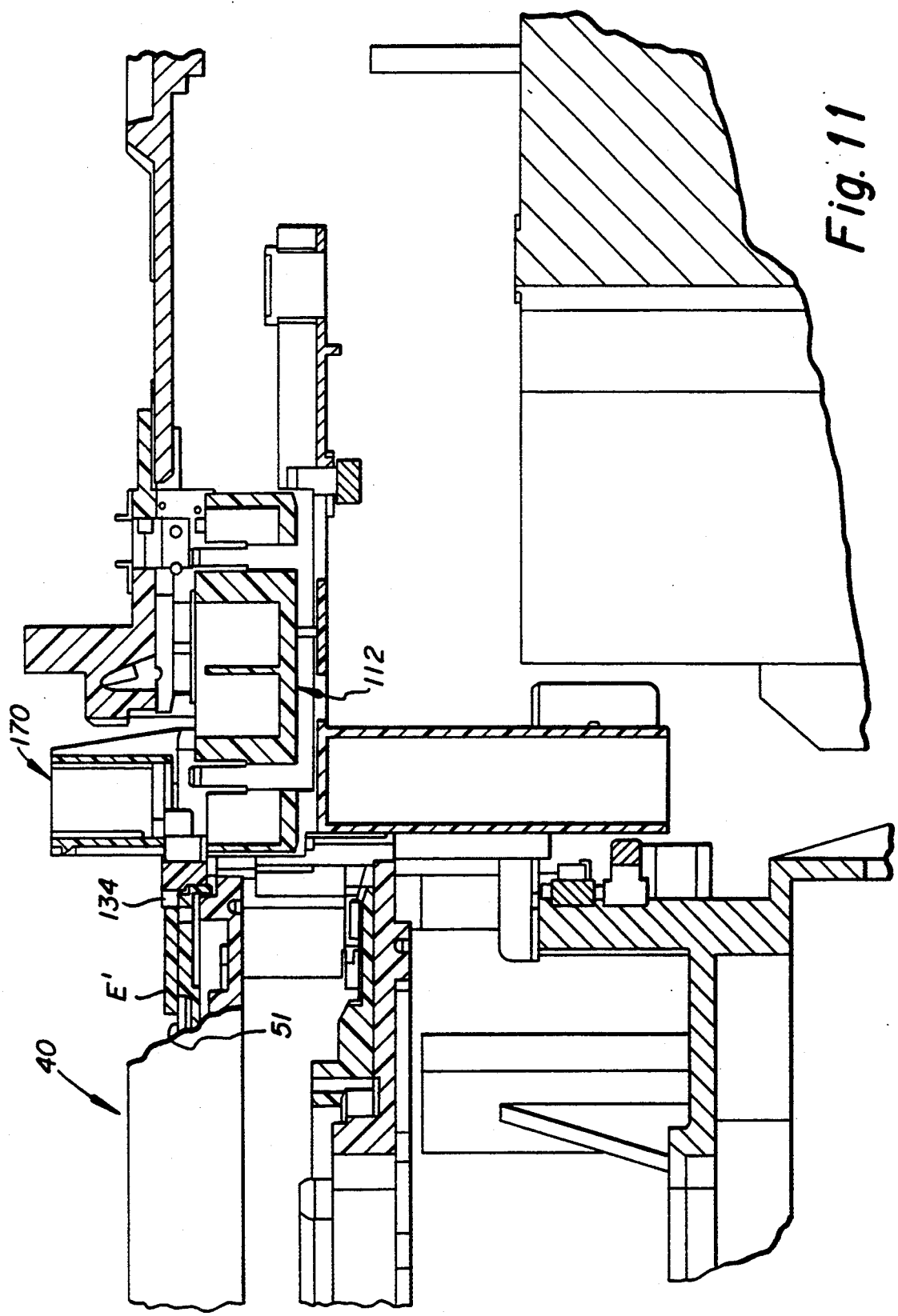

Next, gear 114, FIG. 4, is driven by its motor to advance carrier 112 to the left, FIG. 10, to pick element E' off support 202 and move it directly onto support 51 of incubator 40, FIG. 11. Although FIG. 10 shows the parts with slide E' under cover 170, if the slide element is an element E' it does not stop here but continues to its position shown in FIG. 11. It is only in the case of slide elements E that they stop in the position shown in FIG. 10, resting on support rail 164 (and 162), under the action of pinion gear 114 that drives carrier 112.

Figure 12:
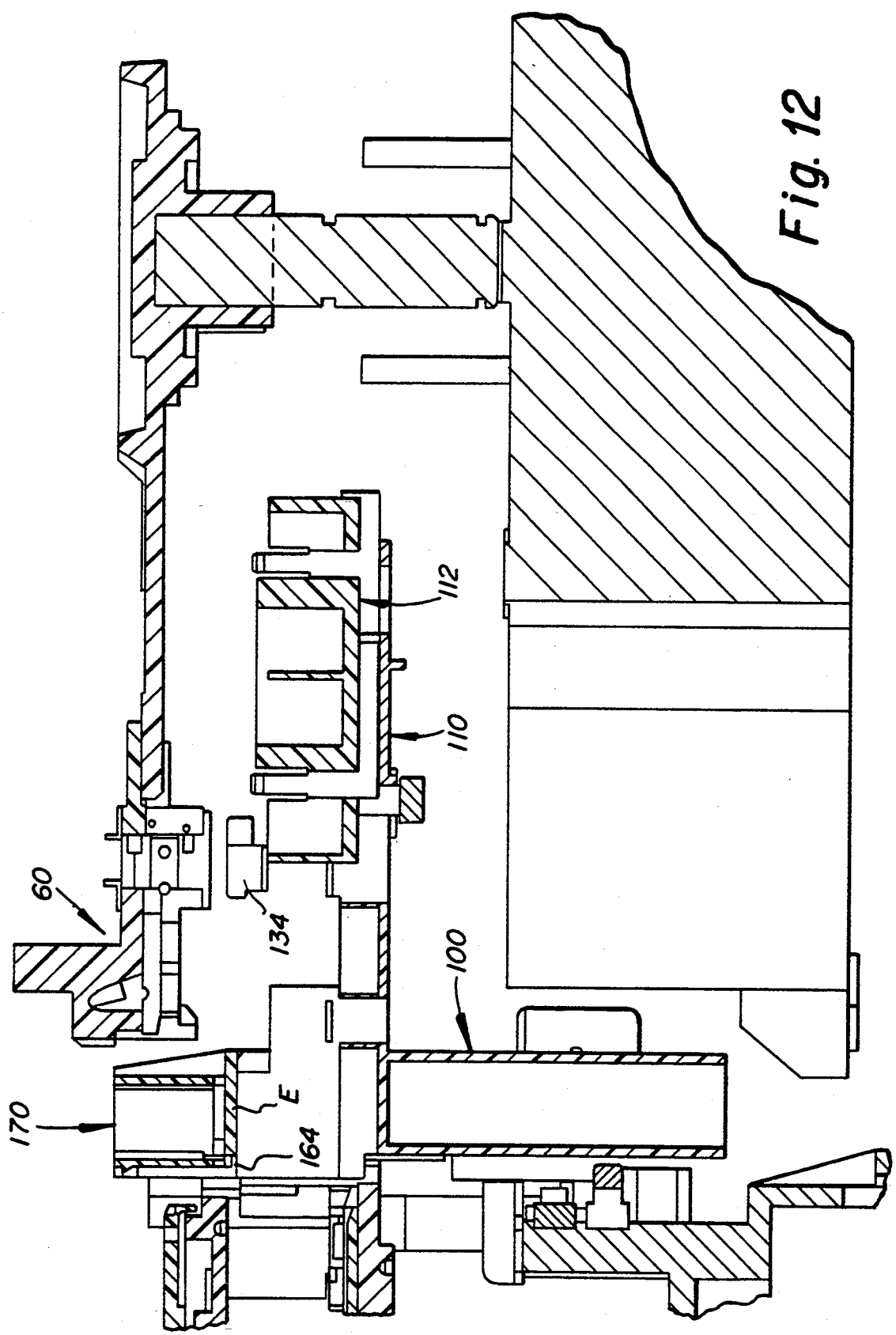

If in fact the slide element is an element E, that is, one destined for incubator 36 rather than 40, it is retained in place on rail 164, FIG. 10, and carrier 112 and blade finger 134 remain positioned behind slide block 60 while the elevator is lowered to incubator 36, FIG. 12.

Figure 13:
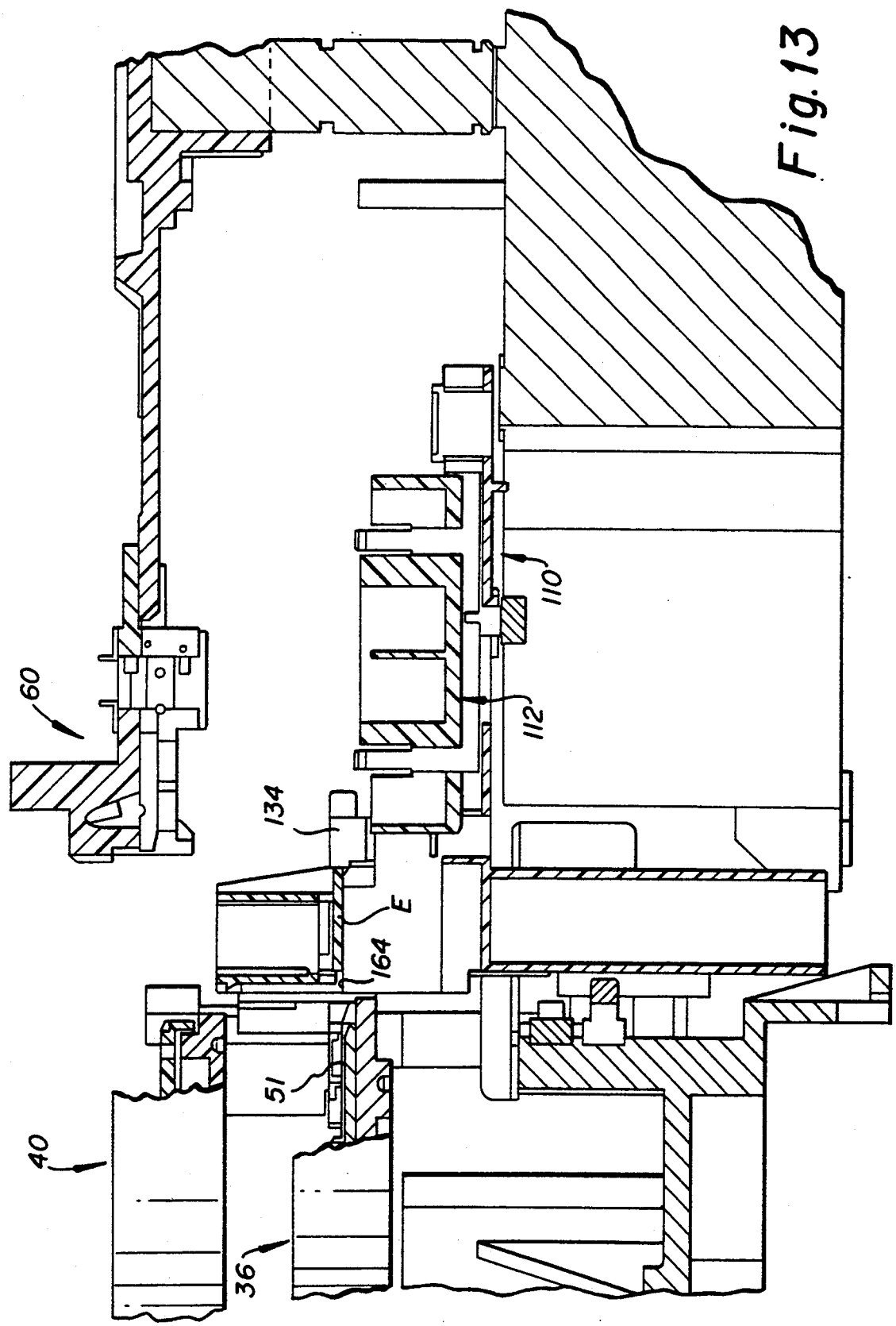

Next, FIG. 13, elevator 100 is lowered via gear 108 and rack 106, FIG. 2, to the lowermost position where support rail 164 is adjacent to and outside of incubator 36. Carrier 112 is advanced from its held position behind element E on rail 164. At this point in the sequence, support rail 164 is in a horizontal plane that is the same as the plane of support 51 of incubator 36.

Figure 14:
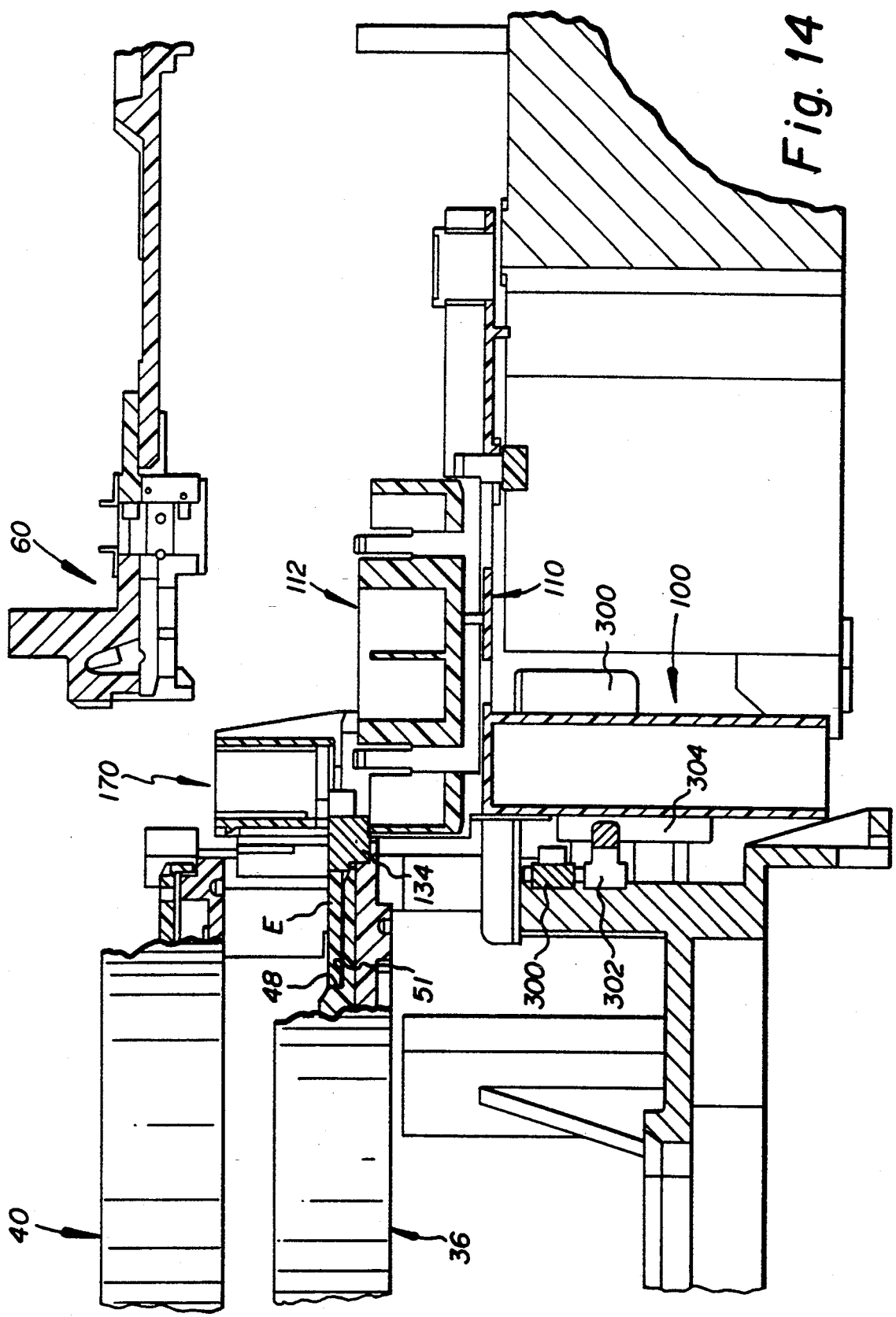

Finally, FIG. 14, carrier 112 is advanced so that fingers 134 et al push element E off support rail 164 onto support 51, up against reference surface 48 it is here that spring 140 comes into play, FIG. 5. To be certain element E has in fact been advanced all the way against reference surface 48, carrier 112 continues to advance slightly farther than nominally necessary. Because blade 130 is free to slide rearwardly against the action of spring 140, as shown in phantom for surface 146, blade 140 does not unduly jam the slide element against the reference surface.

Appropriate sensors are positioned, such as sensors 300, 302, FIG. 14, preferably below incubator 36 to detect from the position of blades such as blade 304, the vertical position of elevator 100. Similarly, a sensor, not shown, is used to detect the position of carrier 112 as it moves through the horizontal plane defined by track 100.

Other Alternative Embodiments

Although the slide distributor is shown located at the height of the upper incubator, so that movement by the elevator is down to the incubator not in line with the distributor, it will be readily apparent that the distributor could be located (not shown) at the height of the lower incubator so that a test element is moved UP to the incubator not in line with the distributor.

Figure 15:
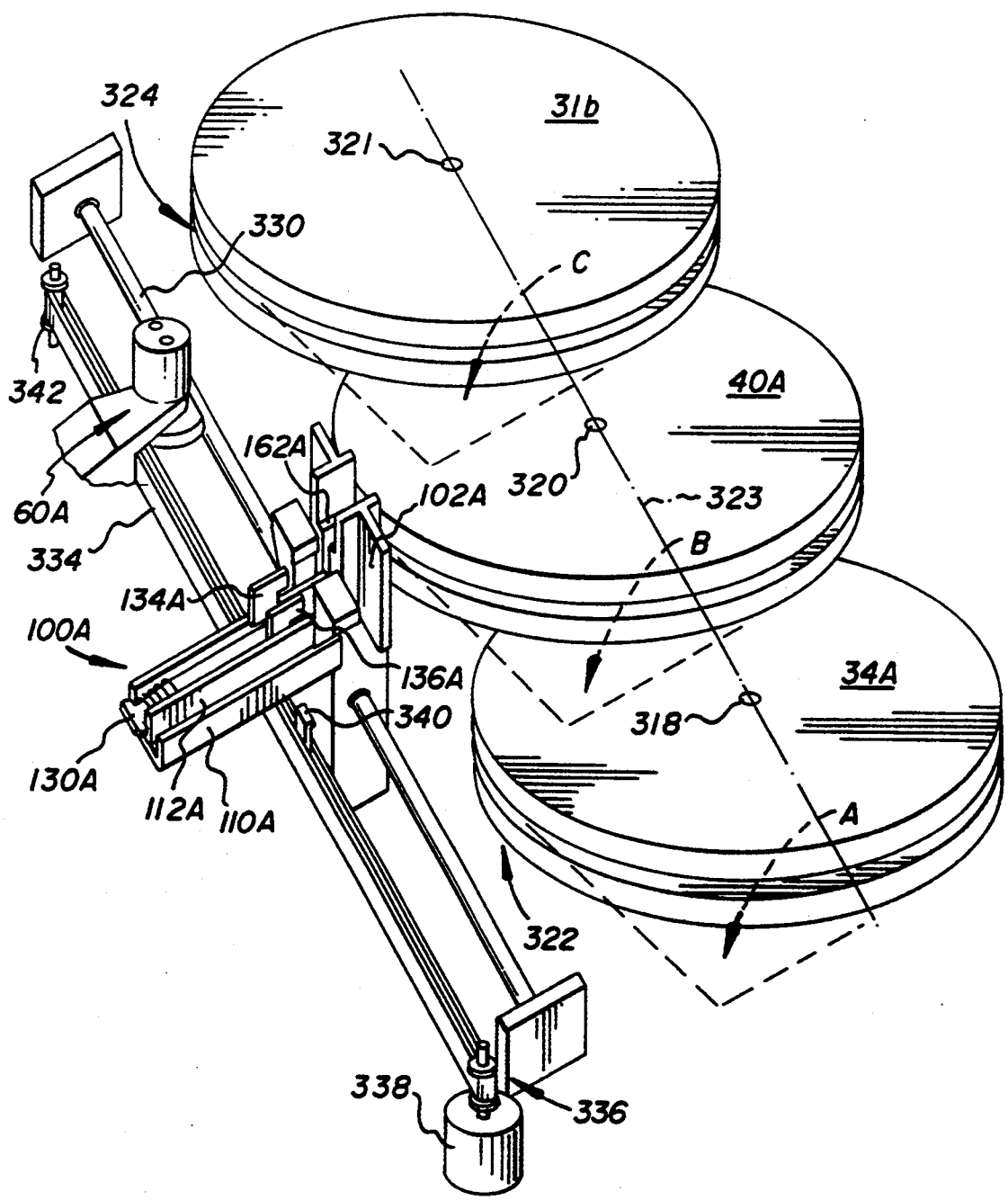
FIG. 15 is a fragmentary isometric view of another embodiment of the invention.

Further, it is not necessary that the elevator of this invention move only up and down, and horizontally, to accommodate only two incubators, one stacked above the other. Thus, as shown in FIG. 15, the elevator can serve three incubators stacked on the diagonal, requiring motion on the diagonal by the elevator as well as in a horizontal plane by the blade carrier. Parts similar to those previously described are given the same reference numeral, to which the distinguishing suffix "A", is appended.

Thus, FIG. 15, not two, but three incubators 34A, 40A, and 316 are stacked vertically with centers 318, 320 and 321 lying along a diagonal axis 323. Their rotors (not shown) thus operate within 3 diagonally offset horizontal planes "A", "B" and "C". This vertical offset of each with respect to the other (instead of being one directly above the other) allows for ease in access to the incubator below an upper one, since the lower one is partially uncovered at all times by the one above it.

As in the previously described embodiment, a slide distributor provides a slide block 60A in a fixed horizontal plane adjacent the incubators, and an elevator 100A comprises a frame 102A supporting a horizontal track 110A on which is reciprocated a carrier 112A having a pusher 130A with fingers 134A, 136A constructed as before (cover 120A not being shown, for clarity). Support rails such as rail 162A are used as before to support a slide element while in the elevator.

However, unlike the previous embodiment, elevator 100A needs to move diagonally rather than straight up and down, so as to be disposed outside of the entrances 322, 324 of incubators 34A and 316 (as well as for incubator 40A, not shown). Accordingly, frame 102A is journalled to slide along a diagonal rail 330 fixed to intersect planes A, B and C just outside of the entrances to the incubator. To drive elevator 100 along rail 330, a conveyor such as endless belt 334 is provided, driven by pulley 336 and motor 338, frame 102A being clipped at 340 to belt 334 so as to travel with the belt. Idler pulley 342 provides the other end for the conveyor. Carrier 112A, though movable on the diagonal with elevator 100A, can still clear horizontal slide block 60A, or enter it, simply by withdrawing or advancing the carrier, respectively, when it is horizontally aligned with the slide block.

With this construction a slide element can be transferred from slide block 60A to support rail 162A, and then the elevator moved diagonally to whatever incubator is intended to receive the slide element. After the elevator is moved into position at the incubator's entrance, pusher fingers 134A, 136A are advanced between support rails (e.g., 162A) of elevator 100A to push the slide into the incubator.

Alternatively (not shown), a second elevator frame can be mounted on rail 330, spaced from elevator frame 102A to increase throughput. Such second frame is raised and lowered by its connection to belt 334, in lock-step with frame 102A.

By way of example, incubators 36A and 40A can be dedicated as described previously, and incubator 320 can be dedicated to colorimetric type slide elements different from those incubated in incubator 36A.

Still another alternative is to replace the rack and pinion drive 106, 108 of FIG. 2, or the endless belt drive 334 of FIG. 15, with a helical or worm gear drive (not shown).

The invention has been described in detail with particular reference to preferred embodiments thereof, but it will be understood that variations and modifications can be effected within the spirit and scope of the invention.

What is claimed is:

1. A combination comprising an analyzer incubator for incubating test elements, and an elevator assembly for positioning and loading test elements from a first position adjacent so said incubator to a second position above or below said incubator;

said incubator comprising a plurality of sites disposed circumferentially for supporting a test element;
   and said elevator comprising a support, means for lowering or raising sad support from said first position to said second position, and for rising or lowering said support, respectively, and
   pusher for pushing a test element onto said support and from said support into said incubator, said pusher comprising a pair of pusher fingers for pushing a test element from said support onto one of said sites and means for moving said fingers with respect to said support,
   said incubator further including a fixed reference surface for abutting against a datum edge of a slide test element and wherein said fingers are mounted on said finger-moving means by a compliant means for biasing said fingers outwardly relative to said finger-moving means, towards said incubator, and to allow said fingers to move back inwardly away from said incubator relative to said finger-moving means when inserting a slide test element datum edge against said fixed surface of said incubator.

2. A combination as claimed in claim 1 wherein said raising and lowering means is selected from the group consisting of an endless belt conveyor and a rack and pinion drive.

3. A combination as claimed in claim 1, further comprising a rack and pinion assembly for moving said fingers.

4. A combination as defined in claim 1, wherein said incubator having said fixed reference surface is dedicated to receiving color-producing slide test elements.

5. A combination as defined in claim 1, wherein said incubator is dedicated to receiving color-producing slide test elements or potentiometric slide test elements, but not both.

6. A combination as claimed in claim 5, and further including sensors fixed relative to said incubator, and means fixed relative to said support for interacting with said sensors to indicate the position of said elevator relative to said incubator.

7. A combination as claimed in claim 5, and further including therein a removable cover mounted at a position spaced above said support by a distance sufficient to accommodate only one slide element between the cover and said support, said cover being biased to stay at said position by a flexible plate and a mating groove and shoulder, one of said shoulder and groove being on said plate.

8. A combination as defined in claim 7, and further including on said cover, anti-skid means for retarding movement of a slide test element onto said support by said pusher.

9. An analyzer for the analysis of analytes in biological fluids, the analyzer comprising a first and a second incubator disposed one above the other, and a slide distributor for moving slide test elements in a fixed horizontal plane to a position adjacent one of said incubators, and further including an elevator for raising and lowering a test element relative to said distributor and relative to first and second loading positions adjacent said incubators, said elevator including a support and a pusher for pushing a slide element from said distributor onto said support and from said support into either of said incubators.

10. An analyzer as defined in claim 9, and further including means for rotating said distributor within said fixed plane.

11. An analyzer as defined in claim 9 or 10, and further including sensors fixed relative to at least one of said incubators, and means fixed relative to said support interacting with said sensors to indicate the position of said elevator relative to said incubators.

12. An analyzer as defined in claim 9, and further including in said elevator a removable cover mounted at a position spaced above said support by a distance sufficient to accommodate only one slide element between the cover and said support, said cover being biased to stay at said position by a flexible plate and a mating groove and shoulder, one of said shoulder and groove being on said plate.

13. An analyzer as defined in claim 12, and further including on said cover, anti-skid means for retarding movement of a slide test element onto said support by said pusher.

14. An analyzer as defined in claim 9, wherein said incubators are disposed one directly above the other, and wherein said elevator includes raising and lowering means comprising a rack and pinion drive.

15. An analyzer as defined in claim 9, wherein said incubators are vertically offset one from the other along a diagonal axis, and wherein said elevator includes raising and lowering means comprising an endless belt conveyor.

* * * * *

UNITED STATES PATENT AND TRADEMARK OFFICE
CERTIFICATE OF CORRECTION

PATENT NO. : 5,419,871

DATED : May 30, 1995

INVENTOR(S) : Martin F. Muszak, et al

It is certified that error appears in the above-indentified patent and that said Letters Patent is hereby corrected as shown below:

Column 7, line 23, after "adjacent" delete "so" and insert --to--.

Column 7, line 28, after "raising" delete "sad" and insert --said--.

Column 7, line 29, after "for" delete "rising" and insert --raising--.

Signed and Sealed this

Third Day of October, 1995

Attest:

BRUCE LEHMAN

Attesting Officer      Commissioner of Patents and Trademarks